(12) United States Patent
Crosby et al.

(10) Patent No.: US 10,471,193 B2
(45) Date of Patent: Nov. 12, 2019

(54) IMPLANTABLE MEDICAL DEVICES

(71) Applicant: TC1 LLC, St. Paul, MN (US)

(72) Inventors: Peter Andrew Crosby, Manly (AU); John Woodard, Turramurra (AU)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 15/969,660

(22) Filed: May 2, 2018

(65) Prior Publication Data

US 2018/0318485 A1 Nov. 8, 2018

Related U.S. Application Data

(60) Continuation of application No. 14/452,455, filed on Aug. 5, 2014, now abandoned, which is a
(Continued)

(30) Foreign Application Priority Data

Dec. 8, 2005 (AU) .................................. 2005906904

(51) Int. Cl.
*A61N 1/36* (2006.01)
*A61M 1/12* (2006.01)
*A61M 1/10* (2006.01)

(52) U.S. Cl.
CPC .......... *A61M 1/122* (2014.02); *A61M 1/1001* (2014.02); *A61M 1/1086* (2013.01);
(Continued)

(58) Field of Classification Search
CPC ........ A61M 1/101; A61M 1/122; A61M 1/12; A61M 2205/3523; A61M 1/1086; A61M 1/10; A61M 1/127; A61M 5/14276; A61M 1/1005; A61M 1/1031; A61M 1/1034; A61M 2027/004; A61M 2205/3344; A61M 2205/3365; A61M 2210/125; A61M 1/1001; A61M 2205/8243; A61M 1/1017; A61M 2205/3507; A61N 1/3787;
(Continued)

(56) References Cited

U.S. PATENT DOCUMENTS 4,248,237 A * 2/1981 Kenny .................. A61N 1/375
607/36
5,211,546 A 5/1993 Isaacson et al.
(Continued)

FOREIGN PATENT DOCUMENTS

CA 2237203 3/1998
EP 1 048 324 11/2000
(Continued)

OTHER PUBLICATIONS

Patent Examination Report No. 1 dated Jun. 20, 2012 in Australian Patent Application No. 2006246529, 3 pages.

*Primary Examiner* — Rex R Holmes
(74) *Attorney, Agent, or Firm* — Squire Patton Boggs (US) LLP

(57) ABSTRACT

An active implantable medical device comprising a therapeutic device, a controller and at least one rechargeable battery, wherein a single hermetically sealed housing encapsulates a therapeutic device, controller and rechargeable battery. A hermetically sealed housing additionally encapsulates a wireless interface and a commutator.

6 Claims, 4 Drawing Sheets

Related U.S. Application Data continuation of application No. 14/010,349, filed on Aug. 26, 2013, now Pat. No. 8,858,416, which is a division of application No. 11/635,283, filed on Dec. 7, 2006, now abandoned.

(52) U.S. Cl.
CPC ............... *A61M 1/127* (2013.01); *A61N 1/36* (2013.01); *A61M 1/101* (2013.01); *A61M 1/1017* (2014.02); *A61M 2205/3507* (2013.01); *A61M 2205/8243* (2013.01)

(58) Field of Classification Search
CPC .......... A61N 1/08; A61N 1/3975; A61N 1/36; A61B 5/0015
See application file for complete search history.

(56) References Cited

U.S. PATENT DOCUMENTS

| | | | |
|---|---|---|---|
| 5,279,292 A | 1/1994 | Baumann et al. | |
| 5,289,821 A | 3/1994 | Swartz | |
| 5,370,509 A | 12/1994 | Golding et al. | |
| 5,569,156 A | 10/1996 | Mussivand | |
| 5,613,935 A | 3/1997 | Jarvik | |
| 5,695,471 A | 12/1997 | Wampler | |
| 5,713,939 A | 2/1998 | Nedungadi et al. | |
| 5,733,313 A | 3/1998 | Barreras et al. | |
| 5,840,070 A | 11/1998 | Wampler | |
| 5,947,892 A | 9/1999 | Benkowski et al. | |
| 5,980,448 A | 11/1999 | Heilman et al. | |
| 6,053,705 A | 4/2000 | Schöb et al. | |
| 6,066,086 A | 5/2000 | Antaki et al. | |
| 6,067,474 A | 5/2000 | Schulman et al. | |
| 6,071,093 A | 6/2000 | Hart | |
| 6,080,133 A | 6/2000 | Wampler | |
| 6,100,618 A | 8/2000 | Schoeb et al. | |
| 6,120,537 A | 9/2000 | Wampler | |
| 6,123,726 A * | 9/2000 | Mori ................... | A61M 1/102 600/17 |
| 6,158,984 A | 12/2000 | Cao et al. | |
| 6,171,078 B1 | 1/2001 | Schöb | |
| 6,217,541 B1 | 4/2001 | Yu | |
| 6,222,290 B1 | 4/2001 | Schöb et al. | |
| 6,223,077 B1 | 4/2001 | Schweizer et al. | |
| 6,227,797 B1 | 5/2001 | Watterson et al. | |
| 6,234,772 B1 | 5/2001 | Wampler et al. | |
| 6,234,998 B1 | 5/2001 | Wampler | |
| 6,240,318 B1 * | 5/2001 | Phillips .................... | A61N 1/08 607/61 |
| 6,264,635 B1 | 7/2001 | Wampler et al. | |
| 6,269,266 B1 | 7/2001 | Leysieffer | |
| 6,278,251 B1 | 8/2001 | Schöb | |
| 6,368,083 B1 | 4/2002 | Wampler | |
| 6,390,969 B1 * | 5/2002 | Bolling .................... | A61M 1/10 600/16 |
| 6,623,420 B2 | 9/2003 | Reich et al. | |
| 6,688,861 B2 | 2/2004 | Wampler | |
| 6,736,770 B2 | 5/2004 | Leysieffer et al. | |
| 6,866,625 B1 | 3/2005 | Ayre et al. | |
| 7,645,225 B2 | 1/2010 | Medvedev et al. | |
| 8,858,416 B2 | 10/2014 | Crosby et al. | |
| 2001/0009645 A1 | 7/2001 | Noda | |
| 2002/0051551 A1 | 5/2002 | Leysieffer et al. | |
| 2002/0161404 A1 | 10/2002 | Schmidt | |
| 2002/0183628 A1 | 12/2002 | Reich et al. | |
| 2004/0084398 A1 | 5/2004 | Breitschwerdt et al. | |
| 2004/0084399 A1 | 5/2004 | Cook et al. | |
| 2004/0234397 A1 | 11/2004 | Wampler | |
| 2004/0236173 A1 | 11/2004 | Viole et al. | |
| 2005/0021100 A1 | 1/2005 | Tsukamoto et al. | |
| 2005/0131487 A1 | 6/2005 | Boveja et al. | |
| 2005/0187594 A1 * | 8/2005 | Hatlestad ............. | A61N 1/3787 607/61 |
| 2006/0069412 A1 | 3/2006 | Ginggen et al. | |
| 2007/0231135 A1 | 10/2007 | Wampler et al. | |
| 2008/0080983 A1 | 4/2008 | Wampler et al. | |
| 2008/0085184 A1 | 4/2008 | Wampler et al. | |
| 2008/0089779 A1 | 4/2008 | Wampler et al. | |
| 2008/0089797 A1 | 4/2008 | Wampler et al. | |

FOREIGN PATENT DOCUMENTS

| | | |
|---|---|---|
| EP | 1 166 820 | 1/2002 |
| EP | 1 354 606 | 10/2003 |
| JP | 2002-224066 | 8/2002 |
| JP | 2004-278375 | 10/2004 |
| WO | WO 95/07109 | 3/1995 |
| WO | WO 97/29795 | 8/1997 |
| WO | WO 01/05023 | 1/2001 |
| WO | WO 2004/052456 | 6/2004 |
| WO | WO 2007/053881 | 5/2007 |

* cited by examiner

IMPLANTABLE MEDICAL DEVICES

CROSS-REFERENCE TO RELATED APPLICATIONS

This application is a continuation of U.S. application Ser. No. 14/452,455, filed on Aug. 5, 2014, titled "IMPLANTABLE MEDICAL DEVICES," now abandoned, which is a continuation of U.S. application Ser. No. 14/010,349, filed on Aug. 26, 2013, titled "IMPLANTABLE MEDICAL DEVICES," issued as U.S. Pat. No. 8,858,416 on Oct. 14, 2014, which is a divisional of U.S. application Ser. No. 11/635,283, filed Dec. 7, 2006, titled "IMPLANTABLE MEDICAL DEVICES," and subsequently abandoned, which claims priority to Australian Patent Application No. 2005/906904, filed Dec. 8, 2005, titled "IMPROVEMENTS TO IMPLANTABLE MEDICAL DEVICES."

FIELD OF THE INVENTION

The present invention relates to improvements to active implantable medical devices. An active implantable medical device may generally include a power source (e.g. a battery), control means (e.g. an electronic circuit) and a means providing the therapeutic action (e.g. an electrode or mechanical pump).

BACKGROUND OF THE INVENTION

An active implantable medical device in which the means providing the therapeutic action is an electrode system (e.g.: a pacemaker or implantable defibrillator) can often be constructed in such a way that all the components with the exception of the means providing the therapeutic action are enclosed inside a single package, which is usually hermetically sealed. However, more complicated active implantable medical devices, or those in which the therapeutic action is mechanical in nature (such as the AbioCor™ fully implantable artificial heart by Abiomed, Danvers, Mass., USA), have in the past, been implanted in multiple components having separate hermetically sealed housings for each implanted component. Typically, the implanted components included a controller, at least one battery, and a therapeutic device. For purposes of this specification, a therapeutic device means a medical device that: actively treats a medical condition of a patient, and requires a power source to operate. Examples of therapeutic devices include, but are not limited to: pacemakers, left ventricle assist devices, cochlear implants, implanted hearing aids, and neural simulators.

As each implanted component generally includes a separate hermetic sealed housing, the implanted medical devices are often bulky and cumbersome. The increased surface area of multiple hermetical sealed housings may lead to increased risk of infection for patients implanted with such a device. Additionally, multiple implanted components add to the manufacturing cost, and may compromise the system reliability.

U.S. Pat. No. 6,269,266—Leysieffer and U.S. Pat. No. 6,736,770—Leysieffer et al describe similar implantable medical devices wherein a therapeutic device and at least one battery are packaged together in hermetically sealed housing and implanted within the body of a patient. However, the devices described within these disclosures are limited to including a therapeutic device with a battery and do not include a controller or device controller within the said hermetically sealed housing. Thereby the devices may require a separate implanted controller with additional housing or the controller may be required to be carried externally relative to the patient.

The present invention aims to or at least address or ameliorate one or more of the disadvantages associated with the above mentioned prior art.

BRIEF DESCRIPTION OF THE INVENTION

In accordance with a first aspect the present invention consists of an active implantable medical device comprising a therapeutic device, a controller and at least one rechargeable battery, wherein a single hermetically sealed housing encapsulates said therapeutic device, said controller and said rechargeable battery.

Preferably, said hermetically sealed housing additionally encapsulates a wireless interface.

Preferably, said hermetically sealed housing additionally encapsulates a commutator.

Preferably, said therapeutic device is a rotary blood pump.

Preferably, a percutaneous lead is connected thereto.

Preferably, a TETS is connected thereto.

In accordance with a second aspect the present invention consists of an active implantable medical device comprising a therapeutic device, a controller, an electrically conductive coil and at least one rechargeable battery, wherein a first hermetically sealed housing encapsulates said controller, said electrically conductive coil and said rechargeable battery.

Preferably, a second hermetically sealed housing encapsulates said therapeutic device.

In accordance with a third aspect the present invention consists of an active implantable medical device comprising a therapeutic device, a controller, an electrically conductive coil and at least one rechargeable battery, wherein a first hermetically sealed housing encapsulates said electrically conductive coil and said rechargeable battery.

In accordance with a fourth aspect the present inventions consists of a controller for a therapeutic device disposed within an active implantable medical device, said controller and said therapeutic device adapted to be powered by at least one rechargeable battery, wherein said controller and said therapeutic device and said rechargeable battery are all housed within a single hermetically sealed housing.

BRIEF DESCRIPTION OF THE DRAWINGS

Embodiments of the present invention will now be described with reference to the accompanying drawings wherein.

BRIEF DESCRIPTION OF THE PREFERRED EMBODIMENTS

Figure 1:
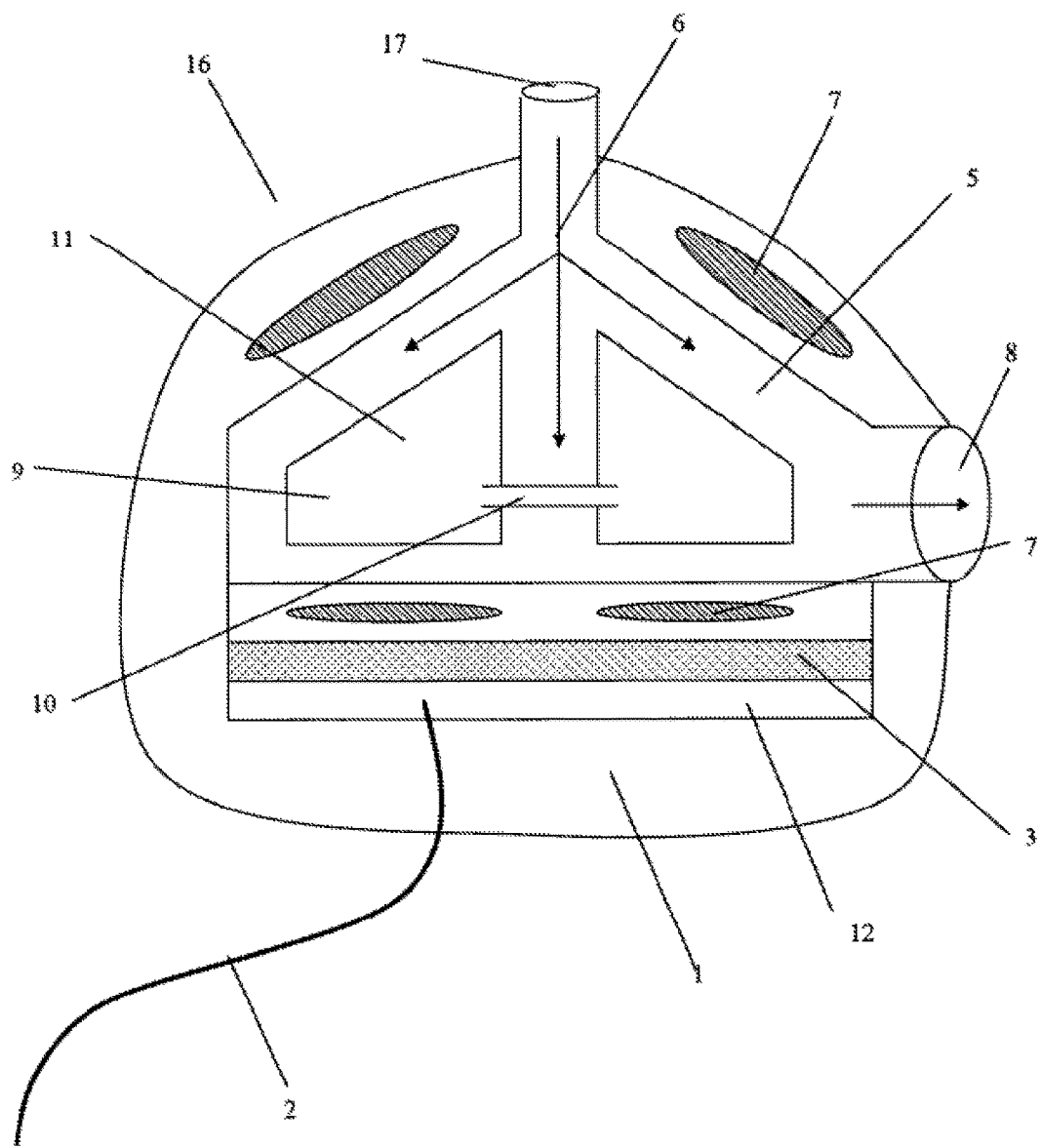
FIG. 1 depicts a front cross-sectional view of a first embodiment of the preferred invention.

In a first preferred embodiment of the present invention, as depicted in FIG. 1, an active implantable medical device 16 is shown. In this embodiment, the active implantable medical device 16 includes rotary blood pump 5 comprising: a DC brushless motor comprising stator coils 7 mounted on opposed sides of an impeller 11. The impeller 11 includes permanent encapsulated magnets (not shown) which interact and cooperate with the stator coils 7, when sequentially energised. Preferably, the stator coils are energised in a manner to facilitate the imparting of a magnetic torque force on the impeller 11 to encourage the impeller 11 to rotate within a cavity of a housing 1. The impeller 11 preferably includes four blades 9 connected by struts 10. The blades 9 preferably include a hydrodynamic bearing surface on the upper and lower surfaces of the blades 9, which provide a means for hydrodynamic suspension when the impeller 11 is rotating at a sufficient speed.

Preferably, blood is urged from an inlet 17 to an outlet 8 by the centrifugal motion imparted by the rotating motion of the impeller 11. The preferred blood path 6 through the blood pump 5 is shown diagrammatically in FIG. 1.

A similar blood pump to the blood pump 5 of the first preferred embodiment is described in U.S. Pat. No. 6,227,797—Watterson et al and the description of that disclosure is herein included within this current embodiment.

In this first preferred embodiment, the active implantable medical device 16 has a hermetically sealed housing 1 that encapsulates: a therapeutic device, namely the mechanical components of the blood pump 5 (i.e. the impeller 11, stators 7, inlet 17 and outlet 8); a rechargeable battery 3, and a controller 12 or pump controller. All of these implanted components are integrated and encapsulated into the one hermetically sealed housing 1.

Preferably, the therapeutic device portions are mechanically operable. An example of a mechanical operable therapeutic device is the pumping motion of the impeller within the rotary blood pump 5.

The hermetically sealed housing 1 preferably encapsulates the therapeutic device portions, the rechargeable battery 3, and the controller 12. This encapsulation allows all of the implanted components of the blood pump 5 to be positioned and mounted within the single housing 1. This significantly reduces the surface area required by the entire active implantable medical device 16 by concentrating the volume of the active implantable medical device 16 in one area. Additionally, the implantation of the active implantable medical device 16 with a patient may be significantly easier and quicker for the clinician as there are fewer objects being implanted. A further advantage may be that having only a single housing 1 reduces the risk of infection, as the risk of infection is generally proportional to the surface area of the active implantable medical device 16.

In the first preferred embodiment of the present invention, the hermetically sealed housing 1 is moulded around the internal components of the active implantable medical device 16. However, the housing 1 may alternatively encapsulate the implanted components by encasing the internal components in an alloy shroud, preferably titanium alloy, which is hermetically sealed by welding.

Preferably, the controller 12 receives instructions, data and power via a percutaneous lead 2 which exits the patient and electrically connects to an external power source (not shown in FIG. 1) or external controller (not shown in FIG. 1). The controller 12 also includes a commutator circuit and sequentially energises the stators 7 to produce the rotational torque drive force on the impeller 11 in accordance with a speed signal derived by the controller 12. The controller 12 also is electrically connected to the rechargeable battery 3. The controller 12 uses the rechargeable battery 3 as a means for storing an electrical charge so that if the percutaneous lead 2 is disconnected the pump may continue to operate. Preferably, the rechargeable battery 3 is charged when the percutaneous lead 2 is connected to an external power source.

Preferably, the controller 12 may operate in a manner similar to the control method described in U.S. Pat. No. 6,866,625—Ayre et al. and the description of this disclosure is herein included within the present specification.

Preferably, the rechargeable battery 3 may include at least one rechargeable battery and this rechargeable battery may be of any type. Preferably, the type of battery included within the active implantable medical device 16 is a Lithium Ion rechargeable battery supplying a 12V power supply.

Figure 2:
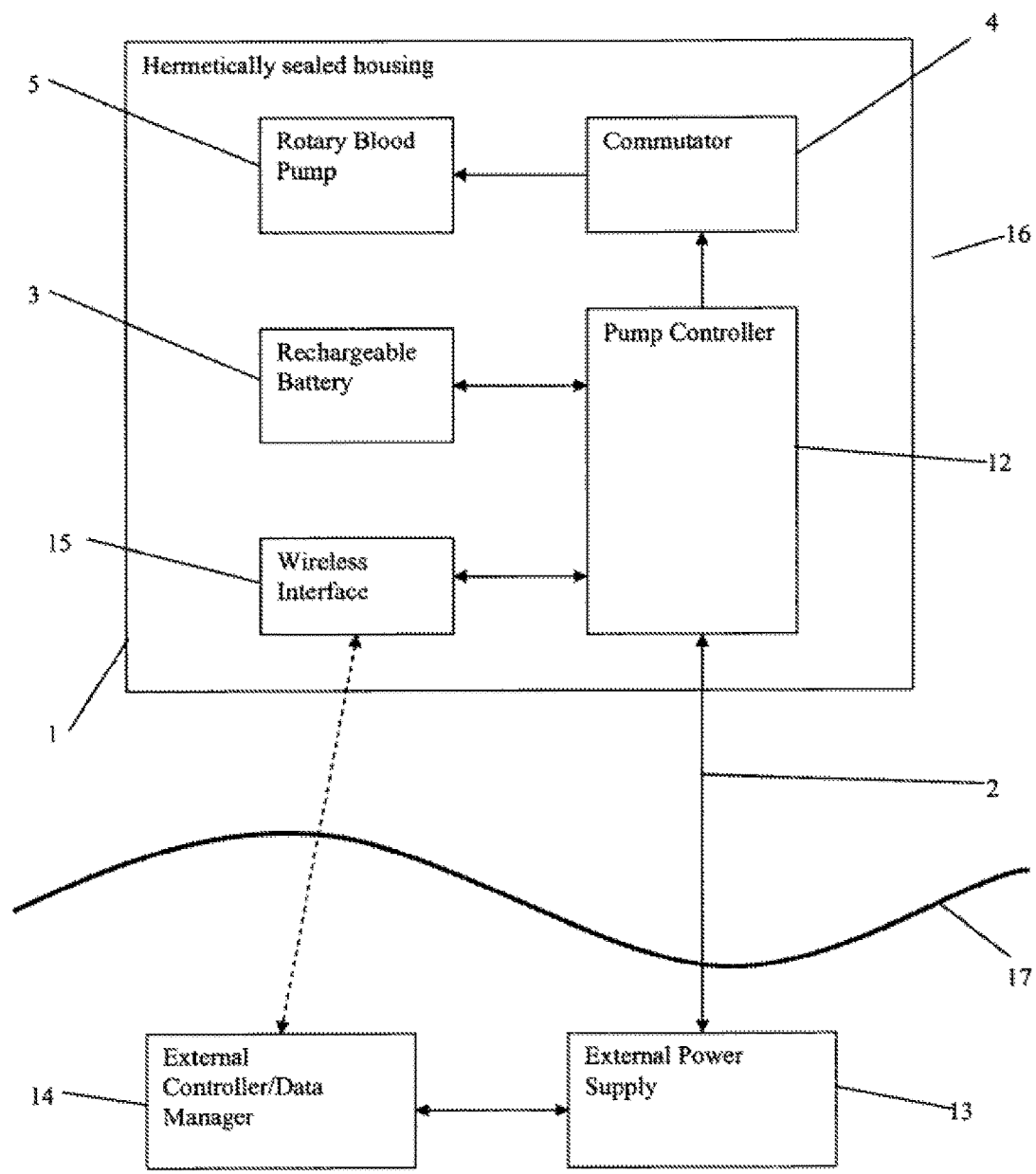
FIG. 2 depicts a schematic view of a second embodiment of the preferred invention.

A second preferred embodiment, similar to first preferred embodiment, is depicted in FIG. 2. In the second preferred embodiment, the rotary blood pump 5 is driven by a commutator 4 which receives a drive signal from the pump controller 12.

Preferably in the second embodiment, the pump controller 12 may be able to selectively switch between the two power sources depending on the circumstances and the power requirements of the active implantable medical device 16.

Additionally in the second preferred embodiment, the commutator circuit 4 is shown as a separate component within the hermetically sealed housing 1. The commutator circuit 4 in this embodiment is also maintained and controlled by the pump controller 12.

FIG. 2 also depicts diagrammatically the manner by which the percutaneous lead 2 exits the skin layer 17 of the patient and connects to an external power supply 13. Preferably, the active implantable medical device 16 is also electrically connected to the external controller and/or data manager 14 (herein referred to as ECDM 14). The ECDM 14 may serve as a backup controller in situations where the pump controller 12 fails. Additionally, the ECDM 14 may manage and store relevant patient or active implantable medical device 16 data. The data may be received from the pump controller 12 through the percutaneous lead 2. Preferably, the ECDM 14 maybe a personal computer or laptop computer running software designed specifically for the purpose of an active implantable medical device control and/or an active implantable medical device data management.

The pump controller 12 may also be electrically connected to a wireless interface 15 as depicted in FIG. 2. The wireless interface 15 is also preferably encapsulated within the hermetically sealed housing 1.

Preferably, the wireless interface 15 is able to transmit and receive data and instructions without the use of the percutaneous lead 2. Thereby the pump controller 12 may be able to wirelessly transmit and receive data and instructions to and from the ECDM 14. Preferably, any wireless interface protocol may be used including, but not limited to: Bluetooth™; Zigbee™; Wi-Fi™; 802.11a, b, & g.

The external power supply 13 maybe a mains power connection which is rectified to provide the required power for the active implantable medical device 16 and/or it may also be rechargeable or long life batteries.

Alternatively, the percutaneous lead 2 may be replaced with the transcutaneous energy transfer system (herein referred to as 'TETS'). TETS generally comprises a two electrical conductive coils positioned either side of the skin layer 17 of a patient. When a first coil energises an electrical current is induced the second coil and whereby allowing the transmission of energy and data via the TETS. The main advantage of TETS is that the patient is not required to have a permanent exit wound from which the percutaneous lead 2 extends. Additionally, one of the said coils may be included within the housing 1 and would further minimise the amount of components to be implanted within a patient.

Figure 3:
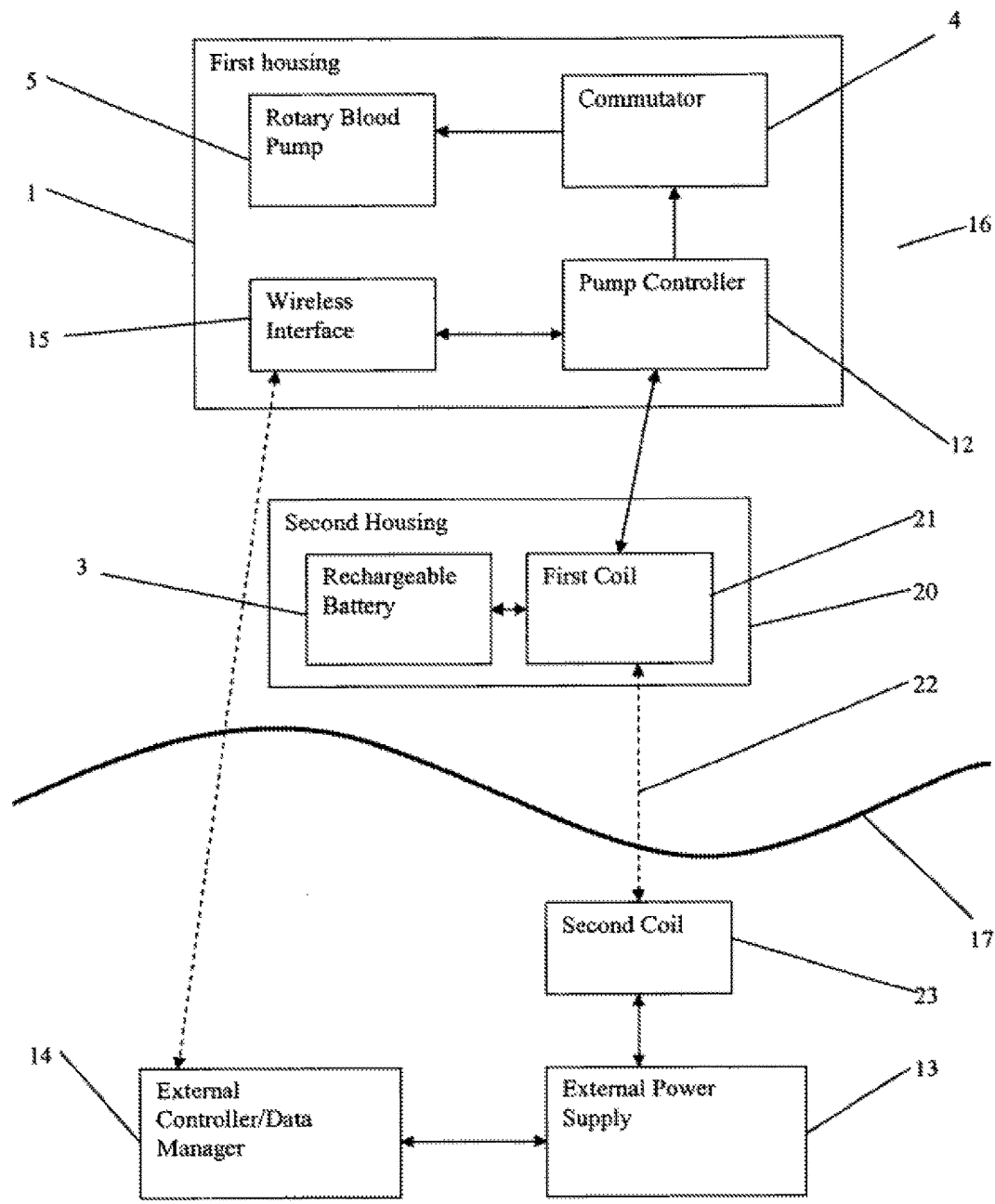
FIG. 3 depicts a schematic view of a third embodiment of the preferred invention.

In a third embodiment of the present invention is depicted in FIG. 3, wherein a therapeutic device is hermetically sealed in a housing 1 with a controller 12, commutator 4 and wireless interface 15. The preferred therapeutic device for use with this second embodiment is a rotary blood pump 5. A battery is housed within a second hermetically sealed housing 20 along with a first electrical conductive coil 21 of a TETS. The first coil 21 implanted beneath the skin layer 17 interacts with a second electrically coil 23 above the skin layer 17. The first and second coils 21 & 23 interact by one coil inducing an electrical current in the opposed coil and thereby allowing the transmission and receipt of electrical energy and also coded data transmission across the transmission link 22 which formed between the first and second coils 21 and 23.

Figure 4:
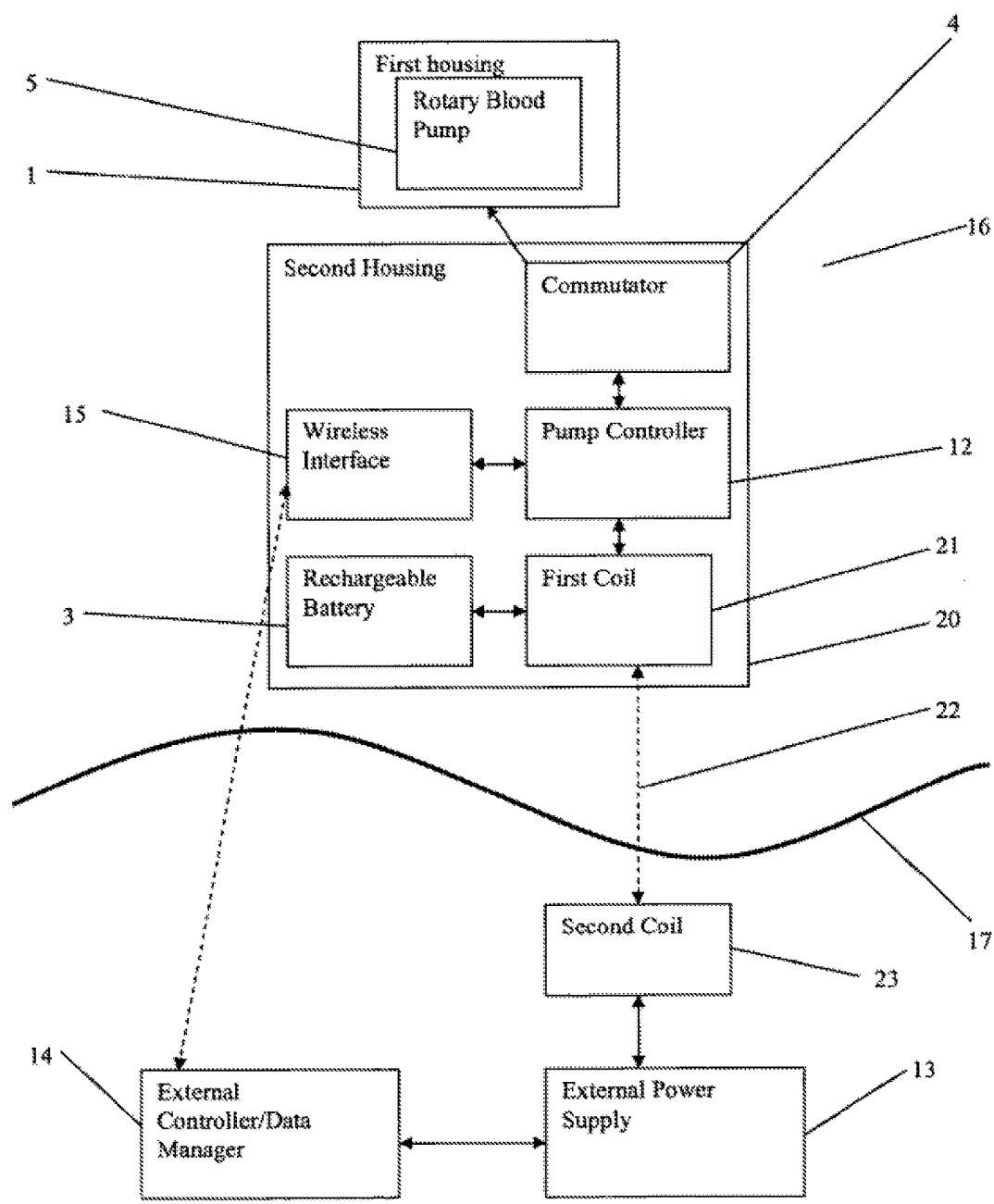
FIG. 4 depicts a schematic view of a fourth embodiment of the preferred invention.

In a fourth embodiment of the present invention is depicted in FIG. 4, wherein a controller 12 and a battery 3 and a first coil 21 of the TETS are hermetically sealed within a second housing 20. A therapeutic device is hermetically sealed within a first housing 1.

The above descriptions detail only some of the embodiments of the present invention. Modifications may be obvious to those skilled in the art and may be made without departing from the scope and spirit of the present invention.

The invention claimed is:

1. A ventricular assist device, comprising:
   a blood pump including stators and an impeller;
   a first controller configured to energize the stators to produce a rotational torque on the impeller;
   at least one rechargeable battery configured to supply power to the blood pump and the first controller;
   a second controller configured to wirelessly energize the stators to produce a rotational torque on the impeller in the event the first controller fails;
   a wireless interface connected to the first controller, wherein the first controller is configured for transmitting data and instructions to/from the second controller via the wireless interface;
   an external power supply, wherein the first controller is configured to switch between the at least one rechargeable battery and the external power supply to satisfy power requirements of the blood pump;
   a first electrical conductive coil for placement beneath a skin layer and a second electrical conductive coil for placement above the skin layer, wherein the first and second coils interact by one coil inducing an electrical current in the opposed coil to thereby allow the transmission and receipt of electrical energy and coded data transmission between the first and second coils;
   a first hermetically sealed housing encapsulating the blood pump, the first controller and the wireless interface; and
   a second hermetically sealed housing encapsulating the at least one rechargeable battery and the first coil.

2. The ventricular assist device of claim 1, wherein the blood pump is a centrifugal blood pump.

3. The ventricular assist device of claim 1, wherein the second controller comprises a controller running software designed for controlling operation of the ventricular assist device.

4. The ventricular assist device of claim 1, wherein the first housing is molded around the blood pump, the first controller and the wireless interface.

5. The ventricular assist device of claim 1, wherein the blood pump, the first controller and the wireless interface are encapsulated within an alloy shroud, which is hermetically sealed by welding.

6. A ventricular assist device, comprising:
   a blood pump including stators and an impeller;
   a controller;
   a commutator separate from and connected to the controller and the blood pump, wherein the commutator is configured to receive a drive signal from the controller and sequentially energize the stators to produce a rotational torque on the impeller;
   a wireless interface connected to the controller;
   an external controller configured for communicating with the controller via the wireless interface, the external controller configured to wirelessly produce a rotational torque on the impeller in the event the controller fails;
   at least one rechargeable battery configured to supply power to the blood pump and the controller;
   a first electrical conductive coil for placement beneath a skin layer and coupled to the at least one rechargeable battery and the controller;
   a second electrical conductive coil for placement above the skin layer, wherein the first and second coils interact by one coil inducing an electrical current in the opposed coil to thereby allow the transmission and receipt of electrical energy and coded data transmission between the first and second coils;
   an external power supply, wherein the controller is configured to switch between the at least one rechargeable battery and the external power supply to satisfy power requirements of the blood pump;
   a first hermetically sealed housing encapsulating the blood pump, the controller, the commutator and the wireless interface; and
   a second hermetically sealed housing encapsulating the at least one rechargeable battery and the first coil.

* * * * *